US009114018B2

(12) United States Patent
Linares et al.

(10) Patent No.: US 9,114,018 B2
(45) Date of Patent: *Aug. 25, 2015

(54) IMPLANTABLE THUMB JOINT ASSEMBLY WITH SPHERICAL INTER-SUPPORT

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 314 days.

This patent is subject to a terminal disclaimer.

(21) Appl. No.: 13/629,764

(22) Filed: Sep. 28, 2012

(65) Prior Publication Data

US 2013/0079886 A1 Mar. 28, 2013

Related U.S. Application Data

(60) Provisional application No. 61/540,207, filed on Sep. 28, 2011.

(51) Int. Cl.
*A61F 2/42* (2006.01)
*A61F 2/30* (2006.01)

(52) U.S. Cl.
CPC ........... *A61F 2/42* (2013.01); *A61F 2002/3064* (2013.01); *A61F 2002/30642* (2013.01); *A61F 2002/30831* (2013.01); *A61F 2002/4251* (2013.01)

(58) Field of Classification Search
CPC .................. A61F 2/4241; A61F 2002/30242; A61F 2002/30673; A61F 2002/30685; A61F 2002/4243; A61F 2002/4246; A61F 2002/4248; A61F 2002/4251; A61F 2002/4253; A61F 2002/4255; A61F 2002/4258; A61F 2/4261; A61F 2002/4271; A61F 2002/4274; A61F 2002/4287
USPC .......... 623/21.11–21.17, 21.19, 23.42, 23.43, 623/23.59
See application file for complete search history.

(56) References Cited

U.S. PATENT DOCUMENTS

| 3,992,726 A | * | 11/1976 | Freeman et al. ............. 623/23.4 |
| 4,231,121 A | | 11/1980 | Lewis |
| 4,276,660 A | | 7/1981 | Laure |
| 4,955,916 A | | 9/1990 | Carignan et al. |
| 5,133,761 A | | 7/1992 | Krouskop |
| 5,147,386 A | | 9/1992 | Carignan et al. |
| 5,290,314 A | | 3/1994 | Koch et al. |
| 5,507,822 A | | 4/1996 | Bouchon et al. |
| 5,782,927 A | * | 7/1998 | Klawitter et al. .......... 623/21.15 |
| 6,099,571 A | | 8/2000 | Knapp |

(Continued)

*Primary Examiner* — Bruce E Snow
*Assistant Examiner* — Brian Dukert
(74) *Attorney, Agent, or Firm* — Gifford, Krass, Sprinkle, Anderson & Citkowski, P.C.; Douglas J. McEvoy

(57) ABSTRACT

A multi-component thumb joint assembly incorporated into reconditioned end surfaces established between upper metacarpal and opposing lower proximal phalanx bones. A first component is anchored into a reconditioned end surface of the metacarpal bone and exhibits a first exposed support surface. A second component is anchored into a reconditioned end surface of the proximal phalanx and exhibits a second exposed support surface. An intermediate and spherical shaped component is supported in at least one of eccentric or rotational fashion between the first and second anchored components.

5 Claims, 4 Drawing Sheets

(56) References Cited

U.S. PATENT DOCUMENTS

| | | |
|---|---|---|
| 6,159,247 A | 12/2000 | Klawitter et al. |
| 6,383,223 B1 | 5/2002 | Baehler et al. |
| 6,423,097 B2 | 7/2002 | Rauscher |
| 6,454,808 B1 | 9/2002 | Masada |
| 8,021,431 B1 | 9/2011 | Townley |
| 8,167,953 B2 | 5/2012 | Warburton |
| 8,366,785 B1 | 2/2013 | Townley |
| 8,377,142 B2 | 2/2013 | Trail et al. |
| 2005/0049716 A1* | 3/2005 | Wagener et al. .............. 623/23.5 |
| 2011/0112652 A1 | 5/2011 | Hansson et al. |
| 2011/0172782 A1 | 7/2011 | Klawitter et al. |

* cited by examiner

IMPLANTABLE THUMB JOINT ASSEMBLY WITH SPHERICAL INTER-SUPPORT

CROSS REFERENCE TO RELATED APPLICATIONS

The present application claims the priority of U.S. Ser. No. 61/540,207 filed Sep. 28, 2011.

FIELD OF THE INVENTION

The present invention discloses an artificial joint assembly, such as is particularly configured for employing as a retrofit thumb joint, and which combines multiple artificial components incorporated into first and second reconditioned joint defining surfaces for providing increased wear life in tandem with evenly distributed wear pattern/profile as well as enhanced flexibility and mobility.

BACKGROUND OF THE RELEVANT ART

The prior art is documented with examples of joint implants including those applicable to replacing the human thumb. Examples of these include the carpometacarpal joint arthroplastic implant, jig, kit and method depicted in U.S. Pat. No. 8,167,953 to Warburton and in which a first base articulating surface is configured to articulate against a trapezium implant articulating surface.

Klawitter, US 2011/0172782, depicts a hemi-arthroplasty joint replacement implant for the base of the first metacarpal of the CMC (carpometacarpal) joint in which a spherical head articular surface is exhibited to the implant mounted to the trapezium. Additional examples of replacement joint prosthesis of a related nature and which exhibit some form of spherical or ball shaped articulating support are shown in each of US 2011/0112652, to Hansson, or U.S. Pat. No. 4,276,660, to Laure.

SUMMARY OF THE PRESENT INVENTION

The present invention discloses a multi-component thumb joint assembly incorporated into reconditioned end surfaces established between upper metacarpal and opposing lower proximal phalanx bones. The assembly includes a first component anchored into a reconditioned end surface of the metacarpal bone and exhibiting a first exposed support surface.

A second component is anchored into a reconditioned end surface of the proximal phalanx and exhibiting a second exposed support surface. An intermediate component is supported in at least one of eccentric or rotational fashion between the first and second anchored components.

Additional features include the intermediate component exhibiting a spherical shaped component. Each of the anchored components can further exhibit a concave surface for supporting the intermediate component. Each of the first, second and intermediate components are further constructed of at least one of a metal, plastic, polymer or composite material.

The spherical shaped component may also have a multi-layer composition including a softer outer layer and at least one harder interior layer. First and second inner layers of the spherical component further establishes an eccentric rotational interface therebetween.

A plurality of surface projecting bearings can be mounted within an innermost spherical shaped portion of the spherical component in a further variant for facilitating the eccentric rotational interface. A grid pattern of lubricating grooves is defined in a surface of an innermost spherical shaped portion of the spherical component in a further variant for facilitating the eccentric rotational interface.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

Figure 1:
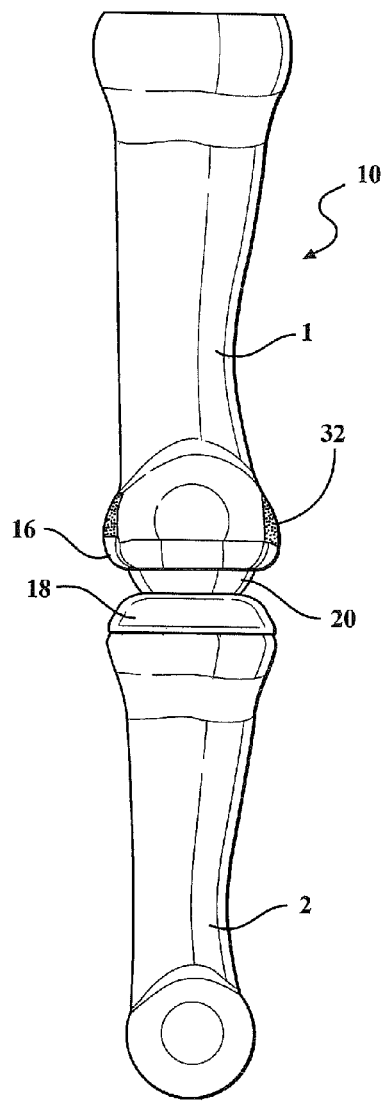
FIG. 1 is a first perspective view of a thumb implant assembly according to the invention.

As will be disclosed with succeeding reference to the several depicted embodiments, the present invention discloses an artificial joint assembly, such as is particularly configured for employing as a retrofit thumb joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's thumb joint existing between lower facing end of the metacarpal bone 1 and corresponding upper end of the proximal phalanx bone 2. Although not depicted in complete detail, the skeleton of the thumb consists of the first metacarpal bone (again at 1) which articulates proximally with the carpus (cluster of wrist bones in base of hand) at the carpometacarpal joint and distally again with the proximal phalanx (again at 2) at what is defined as the metacarpophalangeal joint.

The proximal phalanx also articulates with a distal phalanx (not shown) at a secondary interphalangeal joint. Additionally, there are two sesamoid bones located at the metacarpophalangeal joint. It is further understood that certain applications could in theory include other joint applications, either human or other mammalian.

For purposes of ease and clarify of illustration, the various embodiments depicted further do not include reference to additional necessary components of the thumb joint, such as including associated muscles, tendons and ligaments, the inclusion of which are assumed and which collectively define a functioning and articulating wrist. The associated muscle structure further includes a first grouping of extrinsic muscles (those originating from the forearm), as well as intrinsic muscles (those associated with the hand proper).

A collection of the intrinsic muscle group first includes a ventral forearm muscle, known as a flexor pollicis longus (FPL) which originates on the anterior side of the radius distal to the radial tuberosity and from the interosseous membrane and which passes through the carpal tunnel in a separate tendon sheath, after which lies between the heads of the flexor pollicis brevis, before finally attaching onto the base of the distal phalanx of the thumb. It is further innervated by the anterior interosseus branch of the median nerve.

A collection of three dorsal forearm muscles act on the thumb and initially includes abductor pollicis longus (APL) originating on the dorsal sides of both the forearm ulna and radius bones, and from the interosseous membrane. Passing through the first tendon compartment, the APL inserts to the base of the first metacarpal bone. A part of the tendon reaches the trapezium, while another fuses with the tendons of the extensor pollicis brevis and the abductor pollicis brevis. Except for abducting the hand, it flexes the hand towards the palm and abducts it radially and is innervated by the deep branch of the radial nerve.

A second of the dorsal forearm muscles is the extensor pollicis longus (EPL) which originates on the dorsal side of the ulna and the interosseous membrane. Passing through the third tendon compartment, it is inserted onto the base of the distal phalanx of the thumb. It uses the dorsal tubercle on the lower extremity of the radius as a fulcrum to extend the thumb and also dorsiflexes and abducts the hand at the wrist. It is innervated by the deep branch of the radial nerve.

The third and final of the dorsal forearm muscles is the extensor pollicis brevis (EPB) which originates on the ulna distal to the abductor pollicis longus, from the interosseus membrane, and from the dorsal side of the radius. Passing through the first tendon compartment together with the abductor pollicis longus, it is attached to the base of the proximal phalanx of the thumb. It extends the thumb and, because of its close relationship to the long abductor, also abducts the thumb. It is innervated by the deep branch of the radial nerve.

An associated grouping of tendons of the extensor pollicis longus and extensor pollicis brevis form what is known as the anatomical snuff box which is an indentation on the lateral aspect of the thumb at its base. A radial artery can further be palpated anteriorly at the wrist (not in the snuffbox).

The associated intrinsic muscle group includes four thenar muscles, which are further defined as the group of muscles on the palm of the human hand at the base of the thumb. The abductor pollicis brevis (APB) originates on the scaphoid tubercle and the flexor retinaculum. It inserts to the radial sesamoid bone and the proximal phalanx of the thumb and is innervated by the median nerve.

The flexor pollici brevis (FPB) has two heads, with a superficial head arising on the flexor retinaculum, while a second deep head originates on three carpal (hand) bones including each of the trapezium, trapezoid and capitate. The muscle is inserted onto the radial sesamoid bone of the metacarpophalangeal joint and acts to flex, adduct, and abduct the thumb, and is therefore also able to oppose the thumb. The superficial head is innervated by the median nerve, while the deep head is innervated by the ulnar nerve.

The adductor pollicis also has two heads including a transversal head originating along the entire third metacarpal bone, a secondary oblique head originating on the carpal bones proximal to the third metacarpal. The muscle is inserted onto the ulnar sesamoid bone of the metacarpophalangeal joint and so that it adducts the thumb, and assists in opposition and flexion. The adductor pollicis is innervated by the deep branch of the ulnar nerve.

The opponens pollicis originates on the tubercle of the trapezium and the flexor retinaculum and is inserted onto the radial side of the first metacarpal. It opposes the thumb and assists in adduction and is innervated by the median nerve. Also, the first dorsal interosseous, which is one of the central muscles of the hand, extends from the base of the thumb metacarpal to the radial side of the proximal phalanx of the index finger.

Referring now to FIG. 1, a perspective view is generally shown at 10 of a thumb implant assembly according to an embodiment the invention and which is incorporated between an upper positioned metacarpal bone 1 and lower opposing proximal phalanx bone 2. These bones again collectively defining the metacarpophalangeal joint.

Figure 3:
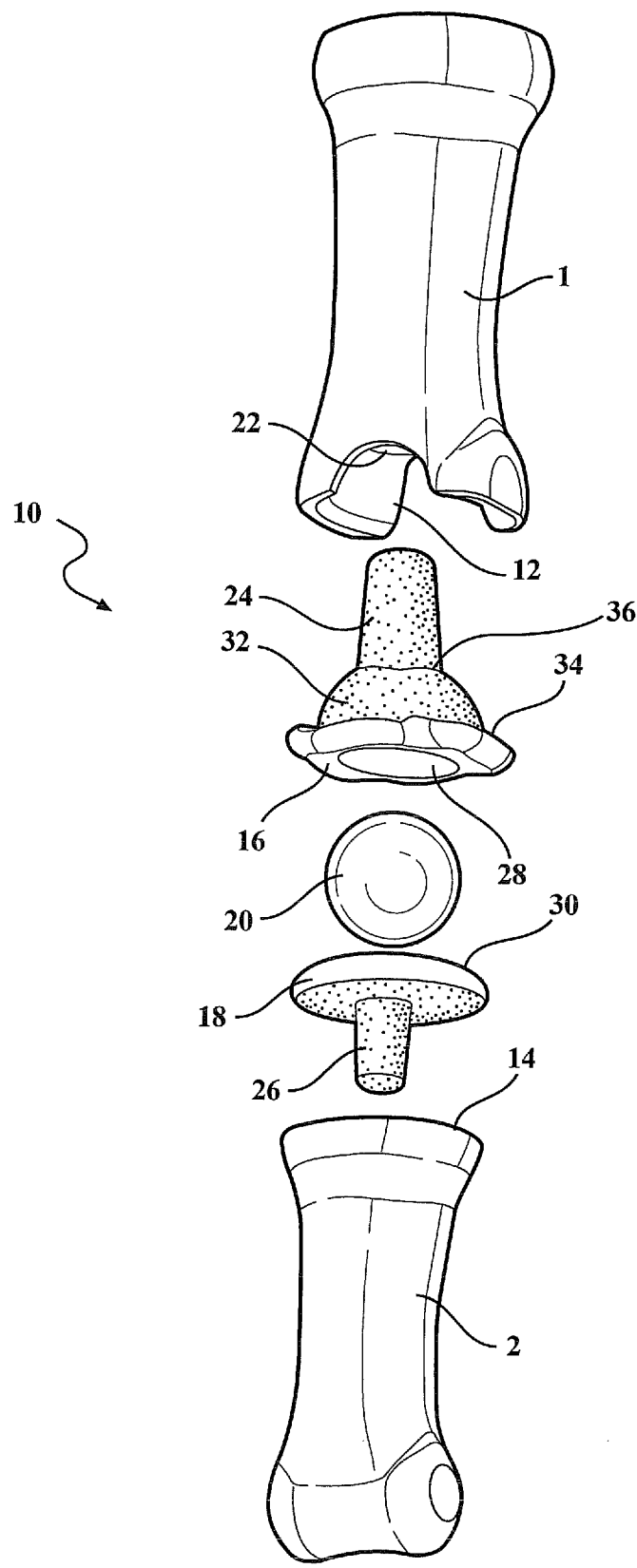
FIG. 3 is an exploded view of the thumb implant assembly of FIG. 1 and better illustrating the reconditioned end-configurations established between the associated metacarpal bone and proximal phalanx bone, combined with end face seating and marrow growth promoting implant support inserts with deep anchorage features in combination with intermediate positioned and eccentrically supported spherical portion.

Having described in some detail the bone construction of the carpus (wrist and hand) and as best illustrated in FIG. 3, each of the metacarpal 1 and proximal phalanx 2 bones are shown in exploded fashion with in situ reconditioning of the bone ends, this illustrated by first reconditioned/recessed end profile 12 configured into the bottom most end surface of the metacarpal 1, as well as opposing upper end facing and recessed/reconditioned profile 14 defined in the upper most opposing facing ends of the proximal phalanx 2. According to one non-limiting surgical procedure, such in situ reconditioning can occur following incision or removal of any remaining damaged bone and/or cartilage associated with the damaged joint and during an appropriate surgical procedure utilizing medical drilling, boring and shaping instruments in order to recondition the joint defining bone ends and to create the desired shaping and profile of the joint. As previously indicated, it is advantageous to refashion the joint end profiles in situ during an appropriate surgical procedure, a further objective being to retain (avoid) or repair, where possible, natural ligament, cartilage and muscle associated with a normal functioning joint.

Although not shown, such reconditioning can be employed with minimal interference to such necessary additional elements of the thumb joint including associated ligaments, muscles and tendons. Without limitation, it is further understood that the joint assemblies described in each of the illustrated variants can be integrated into either of human or synthetic bones (such as which can also contemplate both human and synthetic bones in a single joint application), with such joint assemblies also capable of surgically implanted in either total or partial fashion concurrent with any necessary degree of refashioning or removal of damaged bone or joint.

A set of bone end installable implant portions are depicted at 16 and 18 with each exhibiting a rear facing profile suitable for anchoring into the respective reconditioned end face configurations 12 and 14 defined in the metacarpal 1 and proximal phalanx 2, respectively. Each of the implant portions 16 and 18 are constructed of any arrangement of metal, polymer, plastic, composite or other suitable material, with it further being understood that the individual pairs of components can be arrayed with any pattern of alternating materials, such that the components 16 and 18 being constructed of a first material, with an intermediate and inter-positioned spherical shaped bearing or ball portion 20 positioned therebetween and being constructed of a second alternating material.

Although depicted as a spherical shaped element, the present invention contemplates the thumb joint including any potentially reconfigurable opposing recessed profiles associated with implant portions 16 and 18, and which may further be provided in combination with an alternately (i.e. non-spherical) shaped intermediate component including any type of cylindrical, pseudo cylindrical, oblong, oval ellipsoidal or other smooth shape. In this fashion, the desired wear properties and profiles are adjusted in part based upon the material selection of the individual components with concurrent objectives being both equalization of overall wear patterns established between the respective pairs of components and determining those situations in which metal on metal or plastic on plastic contact between the components is either desired or, more often, not.

A suitable medical adhesive, cement or other fastener can be employed for securing each of the upper implant component 16 into the respective reconditioned joint defining end surfaces 12 of the metacarpal 1, along with the lower implant component 18 being likewise secured into the reconditioned joint defining surface 14 of the proximal phalanx 2. As further best shown in FIG. 3, each of the reconditioned bone ends includes an interior extending aperture (best shown in shallow perspective by central aperture 22 associated with recess end profile 12 of the metacarpal bone 1 with corresponding end communicating aperture associated with the proximal phalanx 2 being hidden due to the angle in which it is presented) and which are formed by a suitable bone drill in order to seat integrally formed and rearward extending anchoring stems including that depicted at 24 associated with a rear mounting profile of the upper insert 16 into the lower end of the metacarpal 1, as well as also shown at 26 associated with rear mounting profile of the lower insert 18 and anchored into the mating interiorly recessed profile and associated drill aperture of the proximal phalanx 2.

Figure 2:
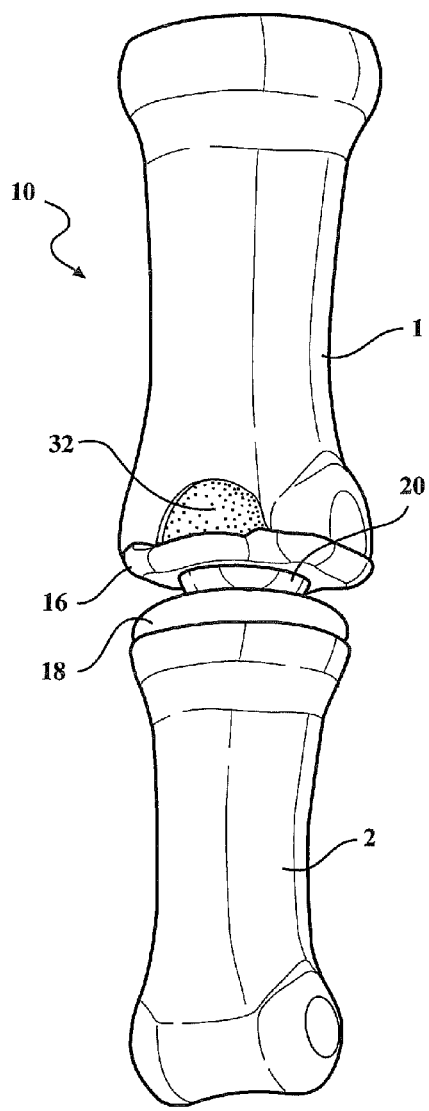
FIG. 2 is a second rotated view of the thumb implant assembly of FIG. 1.

Each of the end face mounted implants 16 and 18 further exhibits a concave exterior facing profile and which includes a more pronounced and substantially hemi-spherical concavity (see at 28 in FIG. 3) defined in the upper anchor 16, with an opposing and lesser pronounced/shallower concave seating cavity 30 (largely hidden from view in FIGS. 1-3) associated with the lower insert 18. Upon securing the implants 16 and 18 within the reconditioned end face locations 12 and 14, these collectively define upper and lower seating locations for supporting the interposed spherical element 20 as again best depicted in the perspectives of FIGS. 1 and 2 and in a designed range of eccentric articulating ranges as permitted by the joint construction. As further previously noted, the concave shaped recess profiles can each be constructed of a smooth lubricant entrained or other polished plastic, composite or metal surface, with the exterior configuration of the spherical support 20 again being constructed of an alternating material, such as to reduce and equalize wear profiles, as well as to enhance operational range and effectiveness.

As again previously indicated, additional configurations of muscles, ligaments, tendons are provided and can include both natural and/or synthetic materials which can be implanted or reconstructed in order to provide a dynamic and long-term implantable assembly. As shown in FIG. 3, the seating or inserting rear faces of the upper mounted implant portion 16 (these including a rear base convex surface 32 of the upper implant 16 which defines an outer lip edge 34 with the perimeter of the implant 16 at a shallowest end, and converging to inwardly extending stem 24 in a deepening direction defined by separating interface 36). Both the upper implant 16 and opposing lower implant portion 18 (again including post 26) can each further include an undercut textured or otherwise roughened consistency as is shown, this contributing to promotion of bone marrow in-growth into the implant portions following such as initial adhesive and seating affixation, such bone growth further contributing to long term retention of the implant.

Figure 4:
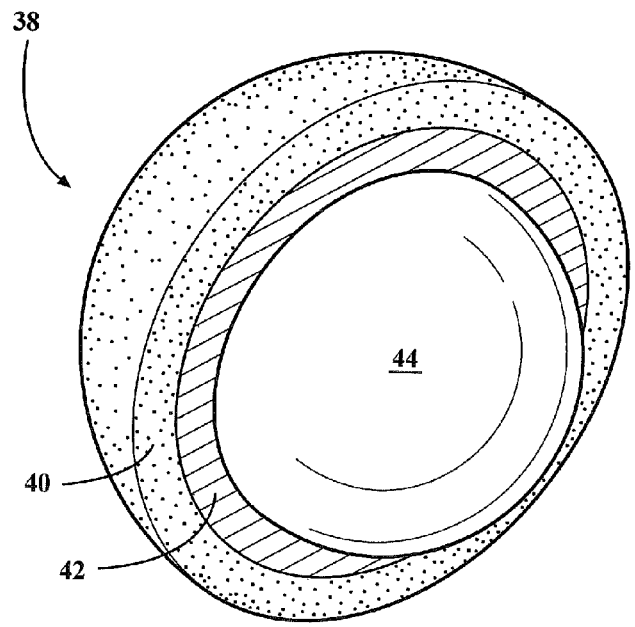
FIG. 4 is a pseudo cutaway view of a spherical shaped intermediate support and which illustrates its multi-material construction with softer outermost shell material and intermediate harder material in cutaway, combined with innermost harder core material in spherical perspective and which further evidences an eccentric rotatable interface established between said intermediate and innermost layers.

Referring now to FIG. 4, a cutaway view is generally shown at 38 of a selected spherical inter-movable support, such as again represented by the spherical ball disclosed in the preceding described variant of FIG. 1. The pseudo cutaway view of FIG. 4 illustrates one non-limiting example of a multi-layer material construction and which includes a softer (typically plastic or plastic composite) outermost material layer 40, an intermediate harder 42 material (typically another plastic), and an innermost harder material 44 (which is depicted in un-sectioned spherical perspective shape and can be of a similar hardness as the intermediate layer 42 as well as potentially including either of a relatively harder or softer material based on the specifics and preferences of the application).

In operation, an eccentric rotatable interface is established between the intermediate 42 and innermost (or core) 44 layers, this typically arising from the compressive aspects exerted on the softest outer shell layer 40 by both the upper and lower associated implants resulting in a degree of inter-rotative offset or eccentric give or play established at the interior interface boundary between the intermediate layer 42 and the inner core 44. The outer compressive exerted forces typically result from any inwardly angular directed force exerted on the intermediate spherical element, and such as is defined as a non-tangential force.

Figure 5:
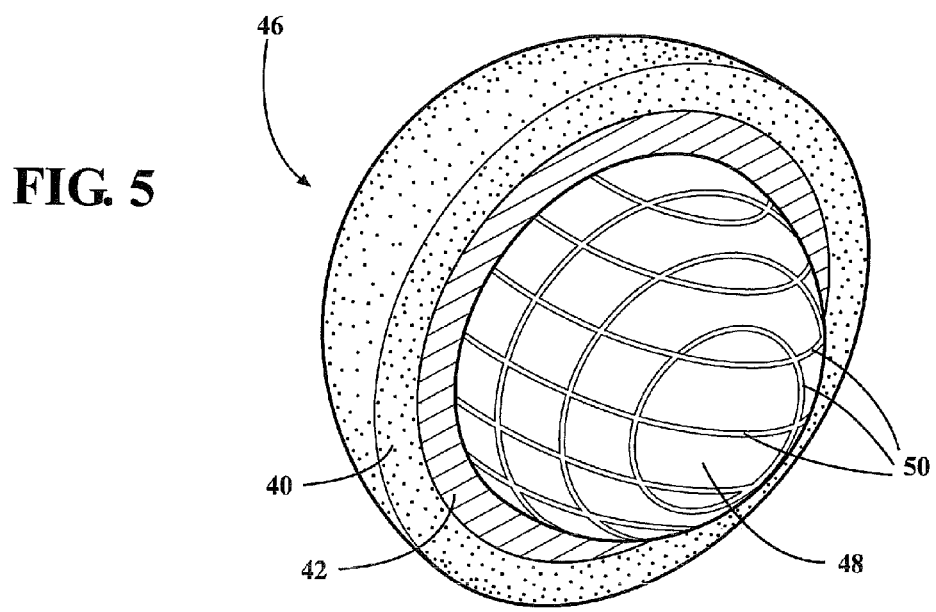
FIG. 5 is a pseudo cutaway view of a spherical shaped intermediate support similar to that in FIG. 4 and further depicting a plurality of lubricant supporting grooves defined in a surface grid pattern associated with the innermost hardened core.

FIG. 5 is a similar pseudo cutaway view, generally at 46, of a spherical shaped intermediate support similar to that in FIG. 5, with identical outer soft shell 40 and intermediate harder shell 42, and in which an innermost core is reconfigured as shown at 48 with a grooved arrangement 50. The grooves 50 can facilitate eccentric motion in the interior boundary defined between layers 42 and 48, in the manner previously described, and/or can also includes entrainment of a volume of lubricant supported within the grooves 50 in a fairly evenly distributed fashion associated with the hardened core 48.

It is also envisioned and understood that the spherical ball, grooves or other supporting structure can include small entrapment channels or pockets for retaining micro particles of debris, either or both plasticized resulting from wear of the implant portions and bone, and such as is further defined as debris osteolysis. The ability to segregate and remove such micro particles (again using the pattern of grooves 64 or other suitable arrangement) assists in extending useful life of the implant along with reducing pain, squeak/noise or other undesirable aspects typical of previous implant designs.

Figure 6:
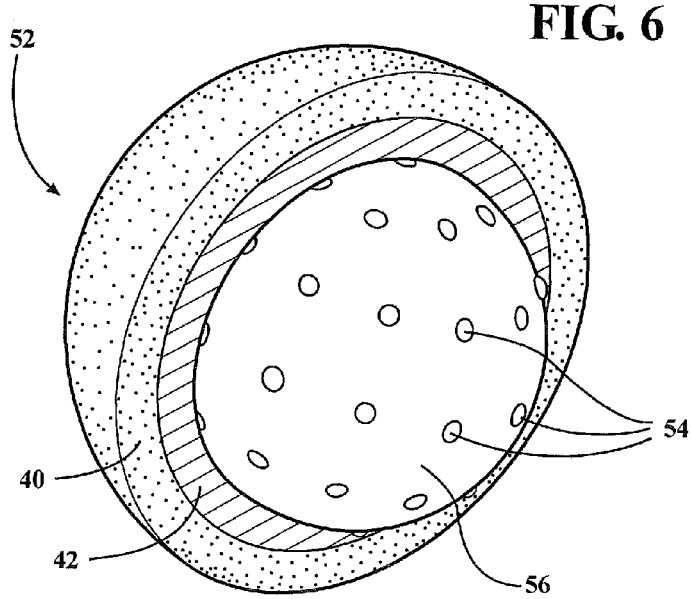
FIG. 6 is a further cutaway view which is again similar to FIG. 4 and further depicting a plurality of substantially surface embedded ball bearings associated with the inner most core.
Figure 7:
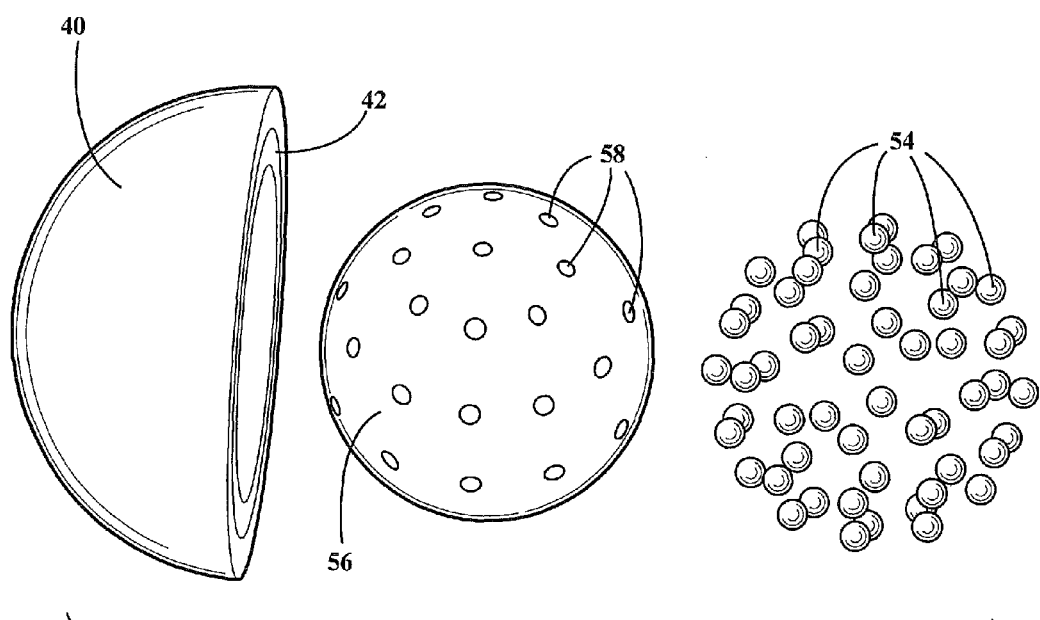
FIG. 7 is an exploded view of the cutaway of FIG. 6 and which better illustrates the arrangement of micro sized ball bearings in combination with the seating locations arranged about the spherical exterior surface of the harder core material.

Referring now to FIG. 6, a further cutaway view is generally shown at 52 which is again similar to FIG. 4 and further depicting a plurality of substantially surface embedded ball bearings 54, such as being constructed of any suitable metal, hard plastic or like material, and which is associated with a further redesigned version of an inner most core 56. As best depicted in the further exploded view of FIG. 7, the ball bearings 54 are separated from the hardened inner spherical core 56, thereby revealing substantially spherical shaped pockets 58 defined across the exterior profile of the core 56 and which substantially seat the individual bearings 54 in a manner which permits the tips thereof (again FIG. 6) to project in a manner which facilitates additional eccentric support motion with respect to the interior interface boundary established with the intermediate later in a manner consistent with the dynamic environments referenced in relation to FIGS. 4 and 6.

Having described my invention, other and additional preferred embodiments will become apparent to those skilled in the art to which it pertains, and without deviating from the scope of the appended claims.

We claim:

1. A multi-component thumb joint assembly incorporated into reconditioned end surfaces established between an upper metacarpal bone and an opposing lower proximal phalanx bone, said assembly comprising:
   an upper implant adapted to being anchored into a reconditioned end surface of the metacarpal bone, said upper implant having a rear base convex surface communicating with an outer lip edge and within which is defined a concave recess, an inward stem extending from an interface with said rear base convex surface and adapted to seat within a recessed interior of the metacarpal bone associated with its reconditioned end surface;
   a lower implant adapted to being anchored into a reconditioned end surface of the proximal phalanx, said lower implant defining a second concave recess, a post extending from a rear of said lower implant and adapted to seat within a recessed interior of the proximal phalanx bone associated with its reconditioned end surface;
   an intermediate spherical shaped component supported between said first and second anchored components and providing articulating support between the upper and lower bones; and
   said spherical shaped component further having a multi-layer composition including a softer outer layer and at least one harder interior layer, said at least one harder interior layer further including first and second inner layers establishing an eccentric rotational interface therebetween.

2. The joint assembly as described in claim 1, each of said upper and lower implants and said intermediate component further being constructed of at least one of a metal, plastic, polymer or composite material.

3. The joint assembly as described in claim 1, further comprising a plurality of surface projecting bearings mounted within an innermost spherical shaped portion established by said first inner layer of said spherical component and facilitating said eccentric rotational interface.

4. The joint assembly as described in claim 1, further comprising a grid pattern of lubricating grooves defined in a surface of an innermost spherical shaped portion established by said first inner layer of said spherical component and facilitating said eccentric rotational interface.

5. The joint assembly as described in claim 1, said upper and lower implants each further comprising textured exterior surfaces adapted to promote bone marrow in-growth in contact with the bone interiors.

* * * * *